United States Patent [19]

Lyons

[11] Patent Number: 5,465,715

[45] Date of Patent: Nov. 14, 1995

[54] POSITIVE LOCKING BIOMEDICAL ELECTRODE AND CONNECTOR SYSTEM

[75] Inventor: Joseph N. Lyons, Wilbraham, Mass.

[73] Assignee: Ludlow Corporation, Exeter, N.H.

[21] Appl. No.: 338,391

[22] Filed: Nov. 14, 1994

Related U.S. Application Data

[63] Continuation-in-part of Ser. No. 106,140, Aug. 13, 1993, Pat. No. 5,372,125.

[51] Int. Cl.$^6$ .................................................... A61B 5/04
[52] U.S. Cl. ............................................ 128/640; 607/152
[58] Field of Search ...................................... 128/640, 641; 607/149, 152; 606/32

[56] References Cited

U.S. PATENT DOCUMENTS

| | | | |
|---|---|---|---|
| 4,653,501 | 3/1987 | Cartmell et al. | 128/640 |
| 4,832,036 | 5/1989 | Cartmell | 128/640 |
| 4,945,911 | 8/1990 | Cohen et al. | 128/640 |

*Primary Examiner*—Lee S. Cohen
*Assistant Examiner*—Brian M. Green
*Attorney, Agent, or Firm*—Richard H. Kosakowski; Holland & Associates

[57] ABSTRACT

A biomedical monitoring or stimulating electrode that adheres to a person's skin is disclosed. The electrode is made of a thin, flat flexible material and includes a die-cut patch having one or more adhesive coatings applied on one side of the patch, a foundation component formed into four integral functional areas, a conductive component made up of an electrically conductive material with three contiguous portions, and a conductive media. A connector interfaces with a tab portion of the electrode. The connector includes an electrically conductive element having an inclined surface upon which the tab of the electrode rests. A slider is movable between two positions such that when in its closed position, the electrode neck and head is trapped in the connector and the slider exerts a force on the inclined surface of a cavity of the connector, providing electrical connection to electrode. Thus, the cavity and firm compression act to prevent the electrode from becoming disengaged from the connector.

19 Claims, 6 Drawing Sheets

POSITIVE LOCKING BIOMEDICAL ELECTRODE AND CONNECTOR SYSTEM

This is a continuation-in-part of U.S. application Ser. No. 08/106140, filed Aug. 13, 1993, now U.S. Pat. No. 5,372, 125, issued Dec. 13, 1994.

BACKGROUND OF THE INVENTION

The present invention relates generally to biomedical electrodes attached to the body for electrical monitoring or stimulating purposes. More particularly, it relates to a disposable biomedical electrode and a corresponding connector that provide a secure, high-integrity, mechanical and electrical interface between a person's skin and a medical instrument.

It is well known that physiological operation of the human heart produces electrical activity that manifests itself in a measurable electrical parameter on the human skin. This electrical activity can be recorded by an electrocardiograph which, by definition, is an instrument that records electric potentials associated with electric currents that traverse the heart. It is also well known that physiological functioning of the brain exhibits electrical activity. To this end, an electroencephalograph is an instrument that records the brain's electrical activity.

Electrical activity of the heart is presented for observation and study by way of an electrocardiogram (ECG), which is a graphical record of the activity, typically the amplitude of the electrical parameter (e.g., voltage) versus time. Electrocardiography is the well-developed science of studying ECGs for medical diagnostic purposes. Electrocardiography is used in a variety of medical procedures to monitor the activity, and diagnose the health, of the human heart.

Further, electromyography is the study of muscular contractions resulting from electrical voltages applied to specific muscle nerves. For example, electromyography can be used when a person is anesthetized in preparation for an operation. Here, specific nerves are stimulated with electricity and simultaneously monitored to see if the anesthetic is working.

In order to sense the electrical signal that is manifested on the human skin, or to provide muscular stimulation, an electrode is typically employed. A sensed electrical signal is transported by an electrical wire from the electrode to the electrocardiograph. The wire is removably attached to the electrode by connector means. A similar system may be used instead for therapeutic electrical stimulation of the muscles and/or nerves. In such instance, the electrocardiograph can be replaced by an electrical stimulating instrument, such as a defibrillator, that transmits electrical current into the body through electrodes. This system may also be used, for example, in electroconvulsive therapy. See U.S. Pat. Nos. 4,736,752 and 5,038,796. In either system, the critical connections are the interface points between the electrode and the human skin, and also between the electrode and the wire cabling. The overall electrical path extends between the human skin, electrode, connector, wire cabling, and medical instrument.

It is known in the early art of electrodes for monitoring or stimulating purposes to use an electrode having a conductive metal surface applied to the skin. The electrodes are held in place, for example, by belts or suction cups. However, these means, because they are inherently uncomfortable, do not lend themselves to long-term usage. An electrically conductive media, such as paste, cream or gel, is applied between the electrode's metal sensing surface and skin to insure a continuous connection therebetween; ideally, across the entire conductive surface area of the electrode. As a rule, direct contacting of an electrode with the skin does not provide sufficient electroconductivity therebetween. The conductive media reduces the air gaps between the electrode and skin, thereby reducing both the amount of impedance of the electrical circuit and any undesirable artifacts or noise in the sensed signal. Such noise can reduce the quality of the signal for diagnostic purposes.

However, this approach suffers from numerous drawbacks, including the fact that the conductive cream or gel is messy to work with and often leaves an undesirable residue. Also, the electrode is not suited for long-term usage. Further, this approach is relatively costly to implement.

It is known in the more recent art of electrodes to use a less-expensive, disposable biomedical electrode. This electrode may comprise a low profile, somewhat flexible pad or substrate having an adhesive surface that is applied directly to the human skin. A portion or all of the adhesive surface may utilize an electrically-conductive gel (e.g., a conductive polymer or hydrogel) that interfaces directly with the skin. The gel is contained in a pad or substrate, typically by impregnating the hydrogel within a porous matrix, such as a woven or non-woven fabric, for example, rayon. Alternately, the hydrogel without a matrix may be disposed within a cavity formed in the pad or body of the electrode or used as a surface coating. See U.S. Pat. No. 4,722,761. The hydrogel is often lightly adherent to the skin, but is sufficiently cohesive throughout so that the pad is easily removed from the skin without leaving any undesirable gel residue thereon when the pad is removed. The tackiness of the hydrogel can be controlled by the amount of cross-linking component in the gel. The gel allows a small amount of relative movement of the electrode with respect to the skin, and is typically able to withstand perspiration, humidity and changes in body temperature without losing its desirable properties. The opposite surface of the pad is attached, usually by lamination, to a conductive metal or conductive circuit that is in physical contact with the hydrogel. See U.S. Pat. Nos. 3,998,215 and 4,515,212. In the alternative, the interfacing element between the conductive metal or conductive circuit and the skin may be comprised of a sponge saturated with an electrolyte solution.

However, the term "hydrogel" usually refers to a gel having a high water content. Thus, the hydrogel will remain solid and in gel form only as long as its water content is retained. Electrolytes also evaporate over time. To prevent evaporation of the water in the hydrogel (which renders the electrode useless), the electrode may be sealed in an aluminum foil package that is impermeable to the ambient environment. See U.S. Pat. No. 3,998,215. Or, the hydrogel may be enclosed within a peelable release paper. See U.S. Pat. No. 5,120,544. This has the effect of increasing the shelf-life of the electrode, but increases the overall cost to manufacture.

Some additional problems encountered with known electrodes include the fact that electrodes with sponges and gel cups tend to be bulky and inflexible, making the electrode uncomfortable and/or undesirably conspicuous. Lack of flexibility can cause the electrode to pull away from the skin, thereby causing discontinuity of the electrical signal. Also, lack of flexibility may cause premature failure and patient discomfort.

Disposable electrodes are typically available with two types of connectors. A first type is referred to as a "snap"

connector electrode. The snap connector comprises an electrically-conductive male extension portion of the electrode that protrudes above the top of the upper surface of the electrode. A corresponding female receptacle is then snapped onto the male extension. The female receptacle is in electrical connection with the electrocardiograph by means of the electrical wiring. See U.S. Pat. Nos. 3,998,215; 3,895,635; 3,696,807; 4,029,086; 3,085,577 and 3,830,229. The snap conductor or fastener is of a two-part construction, and either totally or partially comprises silver, nickel, stainless steel or other conductive metals or metalized plastic. As such, the fastener is a relatively expensive part of the overall electrode. Also, the snap fastener is of considerable mass relative to the remainder of the electrode. Thus, any patient movement may cause the electrode to move relative to the skin of that patient, especially such movements that produce tension in the wire cabling.

A second type of electrode is known as the "tab"-type electrode that has a lateral planar extension of the conductive electrode. The extension is the "tab" to which an alligator clip is usually attached. See U.S. Pat. Nos. 4,852,571; 4,890,622; 4,657,023 and 4,674,512. The wire connection to the electrocardiograph is attached to the alligator-type clip.

Problems with the tab-type electrode include the fact that while the electrode is made to be disposable, the corresponding connector is not. Over time, the gripping action of the clip-on alligator-type connectors tends to weaken. Such weakening degrades the electrical contact between the tab portion of the electrode and the connector, resulting in a degradation of the transmission of the signal from the electrode. Further, if the tab is located on the edge of the electrode, the alligator clip exerts a force on the tab, especially during a patient movement that tugs on the clip, that tends to lift the electrode off the skin, thereby degrading the transmission of the signal from the electrode.

It is to be understood that other variations on the above-described two types of electrodes are well-known.

Accordingly, it is a primary object of the present invention to provide a biomedical electrode system that includes a disposable electrode and corresponding connector that together provide a long-lasting and reliable, high-integrity mechanical and electrical connection between the human skin and a medical instrument.

It is a general object of the present invention to provide a stationary and high-integrity electrical interface between a conductive tab portion of a disposable biomedical electrode and a conductor component portion of a corresponding connector.

It is a further object of the present invention to provide a disposable, inexpensive, flexible, mass-producible electrode that is of relatively thin, flat, and low-profile construction.

It is yet another object of the present invention to provide a biomedical electrode that eliminates the hard protrusions of studs or gel cups in the rigid construction of prior art electrodes.

It is still another object of the present invention to provide a biomedical electrode that is radio translucent and that rapidly dissipates defibrillation charges.

It is still another object of the present invention to provide a biomedical electrode that allows for patient movement and cable strain relief through the flexible characteristics of the electrode.

The above and other objects and advantages of the present invention will become more readily apparent when the following description is read in conjunction with the accompanying drawings.

SUMMARY OF THE INVENTION

To overcome the deficiencies of the prior art and to achieve the objects listed above, Applicant has invented a disposable biomedical electrode that adheres to a person's skin and senses electrical signals present on the skin and conversely provides a pathway for electrical stimulation. The electrode of the present invention interfaces with a reusable connector that securely locks the electrode to the connector and provides an interface to wire cabling that attaches to a medical instrument, such as an electrocardiograph or electrical stimulation device.

In the preferred embodiment, the electrode comprises a thin, flat, flexible electrode that includes a top component in the form of a die-cut patch having one or more adhesive coatings applied entirely on a side of the patch that contacts the skin. The electrode also includes a foundation component comprised of a flexible high-integrity material formed into four integrated functional areas. The areas include a top portion for lifting and positioning the electrode during application and for clean removal when procedures are completed, a center portion located in the center of the adhesive side of the die-cut patch for accommodating a center portion of a conductive component, a stem portion that accommodates an electrical path of the conductive component from the sensor center to a position at the outer periphery of the electrode, and a stem end having a head portion that interfaces with the locking connector of the present invention.

The electrode also comprises a conductive component made of an electrically-conductive material with three contiguous portions, all of the portions being disposed on, or in integral contact with, a surface of the foundation component. A sensor portion is disposed on the center portion of the foundation component and is integral with a neck or pathway portion that leads to the head portion. It is a surface of this end or head portion of the conductive component that contacts and is held securely in place by a connector. The fourth component of the electrode is a conductive media that comprises an electrically-conductive cream, gel, adhesive or other material disposed over the sensor portion of the conductive component. The conductive media interfaces with the human skin to provide electrical conductivity between the skin and the sensor portion of the electrode conductive component.

DETAILED DESCRIPTION OF THE PREFERRED EMBODIMENTS

Figure 1:
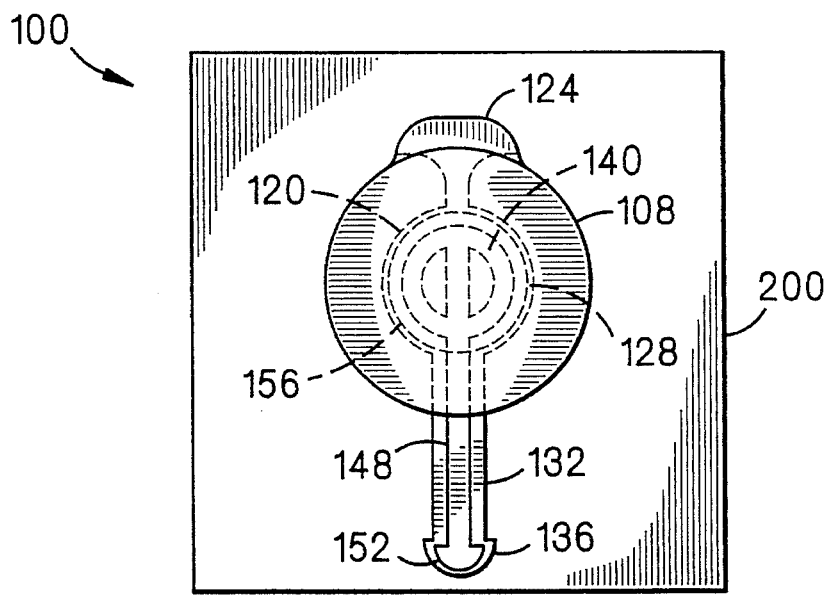
FIG. 1 is a top view of a biomedical electrode of the present invention.

Referring to the drawings in detail, a preferred embodiment of a biomedical electrode of the present invention is illustrated therein and generally designated by the reference numeral 100. The electrode 100 adheres to a person's skin and senses electrical signals present on or through the skin, or impinges electrical signals into the body through the skin. A connector 104 securely locks the electrode 100 to the connector 104 and provides an interface to wire cabling (not shown) that attaches to a medical instrument (not shown), such as an electrocardiograph. The thin, flat electrode 100 includes a die-cut patch 108 having one or more adhesive coatings 112 applied entirely on one side 116 of the patch 108 that contacts the skin. The electrode 100 also includes a foundation component 120 comprised of a high-strength material formed into four integrated functional areas. The areas include a top portion 124, a center portion 128 located in the center of the adhesive patch 108 and attached thereto, a stem (neck) portion 132 that provides a path from the center portion 128 out to the outer periphery of the electrode 100, and a stem end (head) 136 that interfaces with the connector 104. The electrode 100 also comprises a conductive component 140 made of an electrically-conductive material with three contiguous portions, all disposed on the surface of the foundation component 120. A sensor portion 144 is disposed on the center portion 128 of the foundation component 120 and is integral with a neck (pathway) portion 148 that leads to an end (head) portion 152. The fourth component of the electrode 100 is a conductive media 156 comprising, e.g., an electrically-conductive adhesive gel or media, disposed over the sensor portion 144 of the conductive component 140.

The connector 104 includes a slider 160, a conductor component 164 and a base 168, all assembled together. The slider 160 rides in a pair of opposing upper channels 172 in the base 168. A planar surface 176 of a main portion 178 of a cavity 180 formed in the conductor component 164 is inclined at a small angle. The cavity 180 has a narrower neck or channel portion 184 that leads from the main portion 178 of the cavity 180 to an end of the conductor component 164. A bottom surface 188 of the slider 160 is formed in an inclined plane having an identical amount of incline as that of the plane 176 of the cavity 180 of the conductor component 164. The inclined planar surface 188 of the slider 160 has a main portion 192 and a narrower neck portion 196.

In a preferred embodiment, the connector 104 may comprise that disclosed and claimed in U.S. patent application Ser. No. 08/106140, assigned to the same assignee as the present application. The electrode 100 and connector 104 will be sold under the trademark SURELOCK™, by Ludlow Corporation of Exeter, N.H., the assignee of the present invention.

Figure 2:
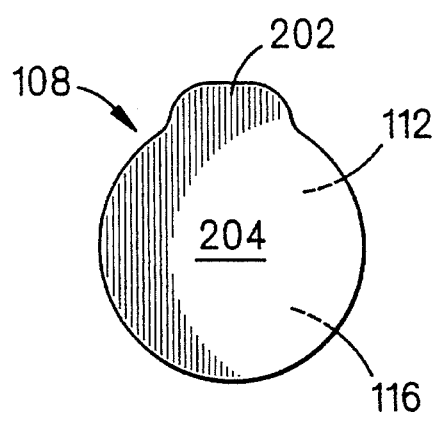
FIG. 2–5 are top views of the four components comprising the electrode of FIG. 1.

Referring to FIGS. 1–5, there illustrated is the biomedical electrode 100 of the present invention. FIG. 1 illustrates a top view of the assembled electrode 100 attached to a release liner 200. FIGS. 2–5 illustrate the four individual components of the electrode. FIG. 2 illustrates a top view of a top component 108 which comprises an adhesive coated, die-cut patch. The patch material may be a film, such as polyester, polypropylene, polyethylene or other suitable material. The material may also comprise, if desired, a woven, non-woven, foam or other flat material which provides good bonding surface for one or more medical grade adhesives 112, conductive and/or non-conductive, disposed on an underside surface 116 of the top component 108. The material chosen should also provide good die-cutting characteristics, as well as the flexibility needed for satisfactory attachment to the human skin. When a film is employed, the film thickness is preferably in the range of 2 mils–15 mils. On the other hand, when a foam is employed, the thickness of the foam is typically 15 to 30 mils. A suitable woven material may comprise, for example, rayon.

Figure 29:
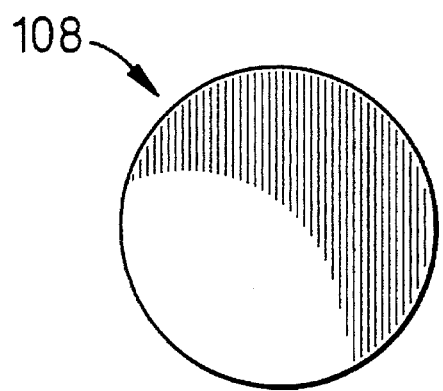
FIGS. 29–32 are top views of alternative embodiments of a patch component of the electrode of FIG. 1.
Figure 30:
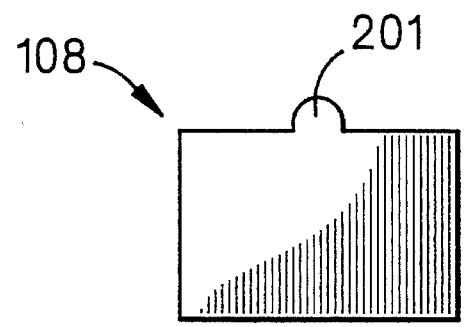
Figure 31:
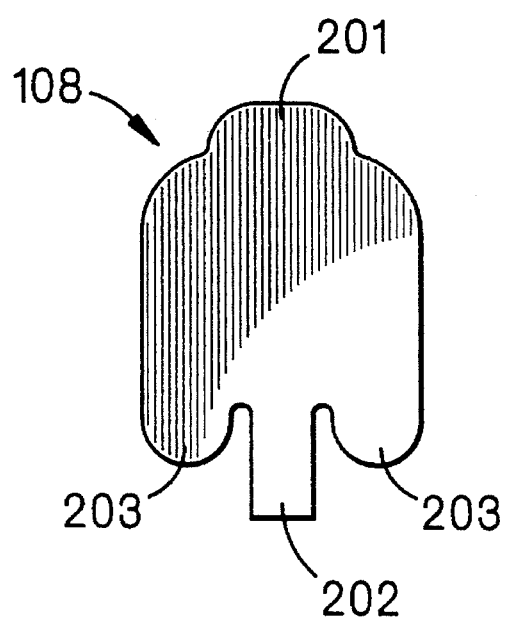
Figure 32:
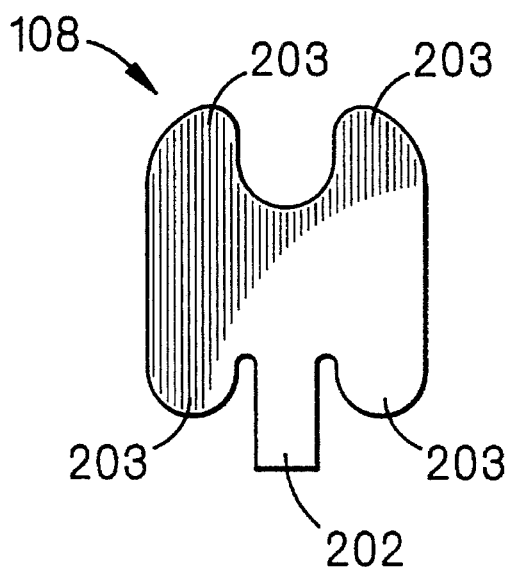

In the preferred embodiment of the electrode 100, the top component 108 is rounded in shape with a protrusion 201 at the top. However, it is to be understood that other shapes may be employed, if desired, without limitation. For example, FIGS. 29–32 illustrate various top views of alternative embodiments of the patch 108. FIGS. 29 illustrates a circular shape; FIG. 30 illustrates a generally square or rectangular shape having a top protrusion 201; FIG. 31 illustrates a "mushroom" shape with both centrally-located top and bottom protrusions 201, 202, side protrusions 203 on the bottom and rounded shoulders on top; and FIG. 32 illustrates an "H"-shape with side protrusions 203 both on the top and bottom, and a bottom protrusion 202. It suffice for the present invention that the top component 108 be die cut into a shape that presents adhesive shear forces whenever the assembled stem portion 132 (described hereinafter) of the electrode 100 has a pulling force applied to it from any direction. This is to keep the electrode 100 securely affixed to the patient's skin. Since the electrode 100 will be used on various ages of humans at different anatomical sites, the patch 108 being of different shapes will provide appropriate adhesive shear forces for the appropriate patient at the appropriate anatomical sites where monitoring is required.

A top surface 204 of the top component 108 is uncoated. However, the underside surface 116 of the top component 108 is coated with one or more medical grade adhesives 112 that adhere to the human skin. The adhesive 112 may comprise a commercially-available hot melt, solvent-based, or water-based adhesive, conductive and/or non-conductive well known in the art, such as the Model 80-1054, provided by National Starch and Chemical Co., of Bridgewater, N.J. In the preferred embodiment, the adhesives 112 cover the entire undersurface 116 of the top component 108 of the electrode 100. However, this is purely exemplary. The type, combination and number of different adhesives 112 chosen depend primarily on characteristics of the patient, such as age and intended anatomical sites for the electrodes 100, as well as on factors such as long-term or short-term monitoring, and the type of medical situation that the electrode 100 is to be used in. For example, an emergency medical situation typically requires a more aggressive adhesive than would be required for a non-emergency situation. Also, some long-term, non-emergency monitoring situations and monitoring of adults typically require a more aggressive adhesive than some short-term monitoring situations or monitoring of infants in general.

Figure 3:
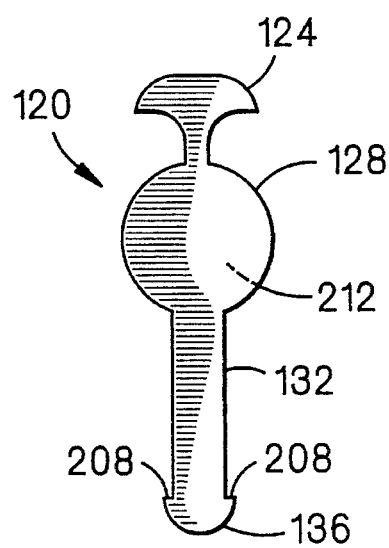

FIG. 3 illustrates a top view of a second component of the electrode—namely, a "foundation" component 120. The foundation component 120 is a skeletal frame that is a multi-purpose component. It is comprised of a flexible, high-strength material, such as polyester, polypropylene or polyethylene, that is die cut into a shape containing four distinct functional areas. The foundation component 120 is of uniform thickness throughout; for example, 2–6 mils.

A first functional area is termed the top portion 124 of the foundation component 120. The top portion 124 provides a lifting tab for easy removal of the electrode 100 from the release liner 200. The tab 124, together with the top protrusion 201 of the patch 108, ensure good positioning of the electrode 100 in the person's hand for effective placement on desired locations on a patient. Alternatively, the top component 108 may not have a protrusion 201 on top. This would leave the tab portion 124 of the foundation component 120 exposed. The tab portion 124 is adequate by itself to perform all of the aforementioned functions. In such an instance, the tab portion 124 may have text or a logo or design printed thereon; for example, the word "lift".

When the desired physiological monitoring or stimulating procedure is completed, the tab 124 and top protrusion 201 of the patch 108 provides for simple, effective removal of the electrode 100 from the skin of the patient. Thus, the easy accessibility of the lifting tab 124, its associated position, and the overall strength of the foundation component 120 all combine to provide added convenience and minimal discomfort during the application, use and removal of the electrode 100.

A second functional area of the foundation component 120 is a center portion 128 that is applied to the adhesive undersurface 116 of the top component 108 of the electrode 100. Typically, the size of the center portion 128 is dictated by the size of the corresponding sensor portion 144 of the conductive component 140 of the electrode 100, described hereinafter. The size of the center portion 128 is also dictated by the surface area of the conductive media 156 necessary for the intended electrical performance criteria of the electrode 100. The conductive media 156 is described hereinafter in greater detail. The center portion 128 of the foundation component 120 thereby supports and holds the conductive component 140 and the conductive media 156 in the center of the top component's adhesive undersurface 116 for reliable positioning of the sensor portion 144 on the skin of the patient. A third functional area of the foundation component 120 is a stem or neck portion 132, which provides a path out from the center portion 128 toward the periphery of the electrode 100. A fourth functional area of the foundation component 120 is the stem end 136 or head portion, which has a pair of shoulders 208 of greater width than the stem portion 132. The significance of the design and shape of the stem portion 132 and stem end 136 will become readily apparent hereinafter in connection with a description of the connector 104.

Figure 4:
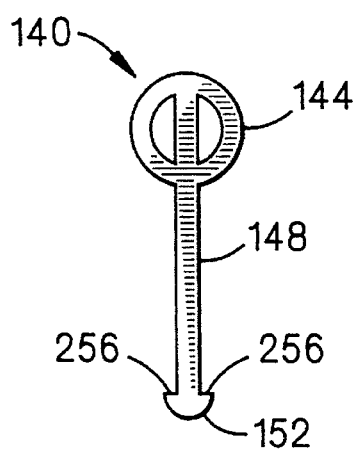

The third component of the electrode 100 is the conductive component 140 that comprises an electrically conductive material disposed on an undersurface 212 of the foundation component 120. A top view of the conductive component 140 is illustrated in FIG. 4. As can be better seen from the assembled complete electrode 100 of FIG. 1, the electrically-conductive material of the conductive component 140 is disposed within the center portion 128, the stem portion 132, and the stem end 136 of the foundation component 120. The electrically-conductive material is typically disposed on the corresponding portions of the foundation component 120 such that the foundation component 120 extends beyond the outer perimeter of the conductive material. However, the outer perimeters of both the foundation component 120 and the conductive material may be equal, if desired, or portions may be equal and other portions may be unequal. The conductive component 140 may either be a die cut conductor, such as aluminum foil, that is laminated onto the undersurface 212 of the foundation component 120, or it may be conductive ink coated directly onto the undersurface 212 of the foundation component 120 using known techniques.

The sensor portion 144 of the conductive component 140 is sized to provide sufficient surface area for the amount of electrical potential of the intended monitoring or stimulating use of the electrode 100. An electrical pathway or neck portion 148 of the conductive component 140 follows the stem portion 132 of the foundation component 120 from the sensor portion 144 of the conductive component 140 out to the periphery of the electrode 100. The pathway portion 148 terminates at an end or head portion 152 that is similar in shape to the stem end or head 136 of the foundation component 120. In the preferred embodiment of the present invention, both the end portion 152 of the conductive component 140 and the stem end 136 of the foundation component 120 have a semi-circular shape. The semi-circular shape provides a relatively large electrical contact area between the conductive component 140 and a conductive surface 176 of a conductor component 164 of the connector 104, described in greater detail hereinafter.

The stem portion 132 of the foundation component 120 gives strength and stability to the corresponding pathway portion 148 of the conductive component 140 attached thereto, thereby providing a secure electrical path from the center of the electrode out to its periphery. This strength rendered by the stem portion 132 also distributes any force applied to the stem portion 132 into the larger center portion 128 of the foundation component 120.

The size and shape of the sensor portion 144 of the conductive component 140 is dictated by the amount of desired impedance of the overall electrode 100, as well as the type and thickness of material comprising the sensor portion. When an electrically-conductive ink is employed, the ink may comprise a galvanic metal, such as silver, and a conductive salt, such as silver chloride. Alternately, the ink may comprise a homogeneous blend of inks, including a first ink comprising a galvanic metal, such as silver, and a conductive salt, such as silver chloride, and a second ink comprising an inert, carbon-based material, such as carbon. An exemplary weight percent of ink components used in a preferred embodiment comprises 0%–90% carbon, 10%–100% silver, and 50%–20% silver chloride. In the alternative, the galvanic metal may be tin, gold or platinum. The conductive salts used in conjunction with these materials are silver chloride, tin chloride, gold chloride, respectively. Also, the inert carbon-based material may be graphite instead of carbon. An exemplary conductive ink is that commercially-available from Acheson Colloids, of Port Huron, Mich.

A conductive salt is ordinarily present in biomedical monitoring electrodes because it resists polarization, enabling the product to meet the A.A.M.I. standards for defibrillation overload recovery. By policy, many medical facilities require that all electrodes meet this standard.

As illustrated in FIGS. 1 and 4, the conductive component 140 is comprised of conductive ink in a preferred embodiment, the ink being distributed in a predetermined pattern that covers a portion of the center portion 128, stem portion 132 and stem end 136 of the foundation component 120. It is to be understood, however, that other patterns of ink may be utilized without departing from the broadest scope of the present invention. The thickness of the conductive ink used is generally in the range of 0.1 to 0.8 mils; however, the thickness varies depending on the composition of the ink, the desired impedance of the electrode 100, and defibrillation recovery requirements.

Figure 5:
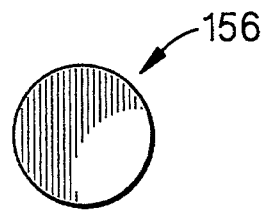
Figure 6:
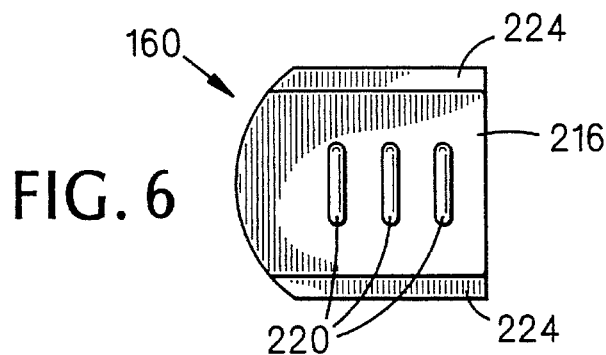
FIGS. 6–10 illustrate various views of a slider component of a connector that interfaces with the electrode of FIG. 1.
Figure 7:
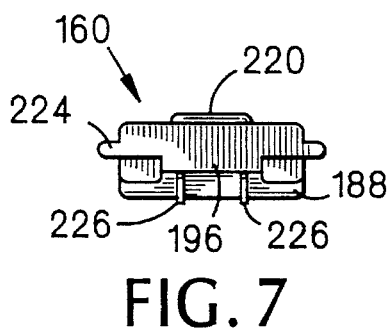
Figure 8:
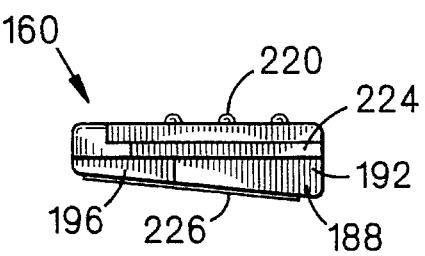
Figure 9:
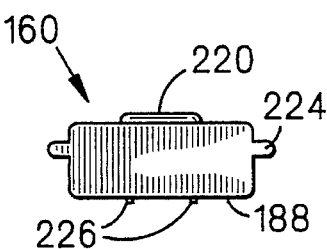

FIG. 5 illustrates a top view of the conductive media 156. The conductive media 156 typically comprises an electrically-conductive cream, gel, adhesive, or other material that, when pressed in place against human skin, provides electric conductivity between the skin and the sensor portion 144 of the conductive component 140. Without limitation, the conductive media 156 may be free-standing on the sensor portion 144 of the conductive component 140, held in place by a cup-like device, in a sponge or saturating an open matrix material. It may or may not have adhesive properties to both assist in the bonding of the electrode 100 to the patient and to reduce electrical artifacts caused by movement between conductive components. In a preferred embodiment of the present invention, the conductive media 156 comprises a medical grade, electrically-conductive hydrogel with adhesive qualities that is commercially available. The conductive media 156 may comprise the Model RG-63B, provided by Ludlow Corporation, of Exeter, N.H., the assignee of the present invention.

It can be seen from the foregoing that FIGS. 2–5 illustrate the individual components of the electrode 100 of FIG. 1 as they are layered together from the top of the electrode 100, or farthest part of the electrode away from the human skin, down toward the actual interface with the human skin. The portion of the electrode 100 that actually contacts the human skin is the non-conductive adhesive 112 disposed on the undersurface 116 of the top component 108 of the electrode 100, as well as the conductive media 156 disposed concentric with the top component 108. The conductive media 156 enhances the conductivity of the electrical signals present on the human skin through the media 156 and into the sensor portion 144 of the conductive component 140. These electrical signals are then brought out through the pathway portion 148 to the end portion 152 of the conductive component 140 where they are transferred to the connector 104, through wiring (not shown) to a biomedical monitoring device, such as an electrocardiograph (not shown). The conductive media 156 also enhances the transfer of electrical signals into the body through the skin.

It should be understood that for the broadest scope of the present invention, the top component 108 is not required. It suffice that the electrode 100 consist of the foundation component 120, the conductive component 140 and the conductive media 156.

FIG. 1 also illustrates a release liner 200 or carrying sheet upon which the assembled electrode 100 is mounted. A function of the release liner 200 is to cover the active adhesive properties of the electrode. That is, the release liner must contain barrier properties to prevent the conductive media 156 from drying out and losing its adhesive and conductive properties. The number of electrodes 100 mounted on a carrying sheet 200 is determined by end use requirements. The release properties of the release liner 200 are brought about by a silicone coating that allows the release of the adhesive 112 applied to the undersurface 116 of the top component 108 and also the adhesive of the conductive media 156, from the release liner 200 without unintentionally delaminating the electrode 100. Such release liners 200 are well known and commercially available and may comprise those available from Daubert Coated Products, of Westchester, Ill.

Referring now to FIGS. 6–16, there illustrated are various views of the three components of the connector 104 utilized with the electrode 100 of the present invention. The three components are a slider 160, a conductor component 164 and a base 168. The slider 160 and base 168 are non-electrically-conductive, while the conductor component 164 is electrically-conductive. The three components may, if desired and without limitation, comprise suitable conductive and non-conductive plastic materials that are injection molded into the desired shape. However, other materials and methods of manufacture may be utilized, if desired.

Figure 10:
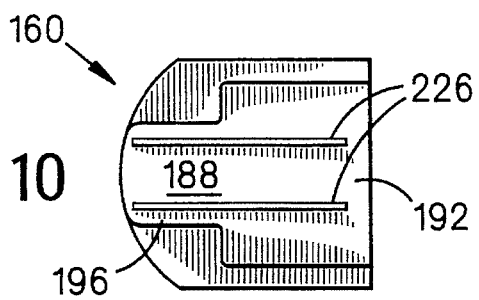

Illustrated in FIGS. 6–10 are top, bottom and three side views of the slider 160. A top surface 216 of the slider 160 has a number of parallel, rectangular protrusions 220 that facilitate movement of the slider 160, such movement described hereinafter in greater detail with respect to an operative example of the connector 104. The slider 160 also includes a planar flange 224 that bisects the entire slider 160. A portion of the bottom surface 188 of the slider 160 is inclined. As best illustrated in FIG. 10, the inclined surface 188 has a narrow neck or tab portion 196 integral with a wider main portion 192. The bottom surface 188 also includes a pair of "rails" 226 protruding therefrom.

Figure 11:
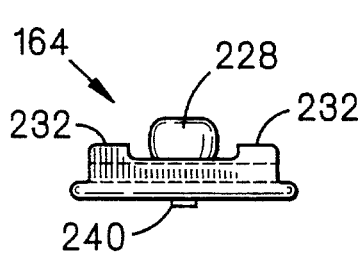
FIGS. 11–13 illustrate various views of a conductor component of the connector of FIGS. 6–10.
Figure 12:
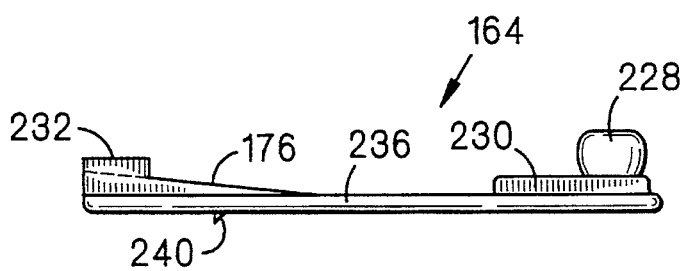
Figure 13:
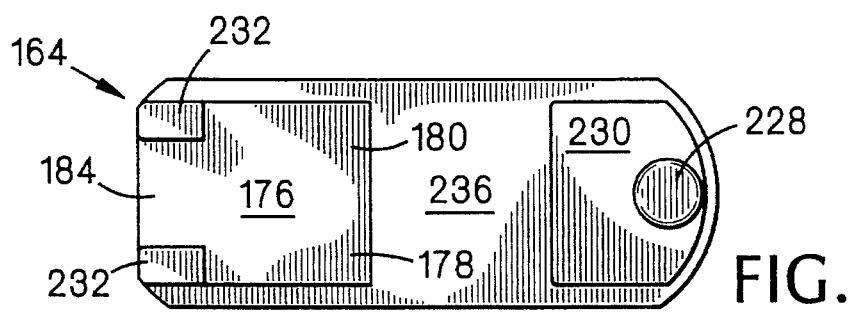

Illustrated in FIGS. 11–13 are a pair of side views and a top view, respectively, of the conductor component 164 of the connector 104. As best illustrated in FIGS. 12 and 13, the conductor component 164 comprises a planar piece of material having a conductive post 228 protruding upward therefrom from a flat, planar mesa 230 formed on the right side of the conductor component 164. Disposed on the left side of the conductor component 164 is a pair of vertical columns 232 rising to a predetermined height above a main planar surface 236 of the conductor component 164. The conductor component 164 also includes a cavity 180 having a main portion 178 and a narrower neck or channel portion 184. The entire cavity 180 comprises a surface 176 that is inclined with respect to the main planar surface 236 of the conductor component 164. The angle of incline of the surface 176 equals the angle of incline of the bottom surface 188 of the slider 160. Further, the width of the neck or channel portion 184 of the cavity 180 approximates the width of the tab portion 196 of the bottom surface 188 of the slider 160. The conductor component 164 also includes a small "nub" 240 protruding from the bottom thereof.

Figure 14:
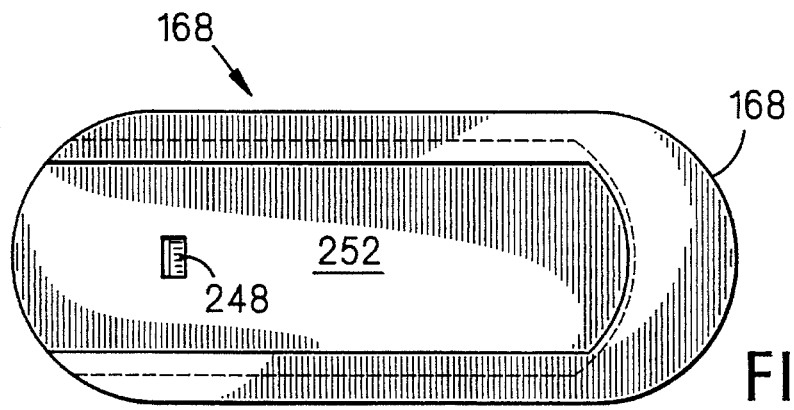
FIGS. 14–16 illustrate various views of a base component of the connector of FIGS. 6–10.
Figures 15, 16:
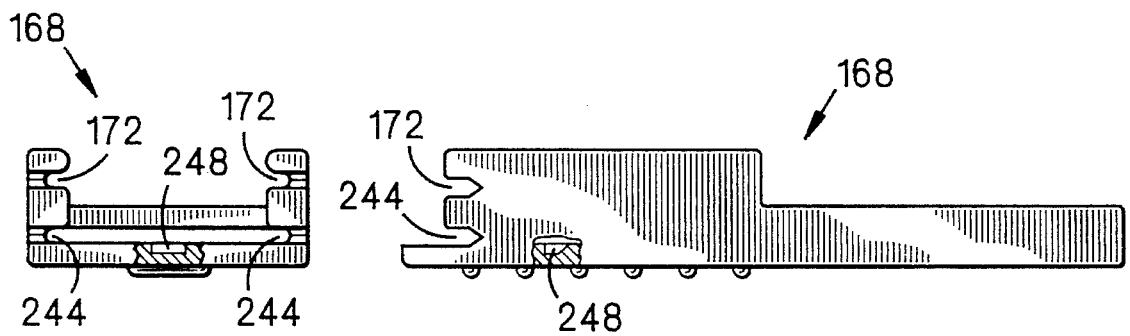

FIGS. 14–16 illustrate a top view and a pair of side views, respectively, of the base component 168 of the connector 104. As can best be seen from the end view of FIG. 15, the base 168 has a pair of opposing "channels" 172 formed therein near the top of the base 168. Also, the base 168 has a pair of opposing lower channels 244 formed therein near the bottom of the base 168. These channels 172,244 extend throughout the entire length of the base 168, as illustrated in FIGS. 14 and 16. Although both pair of channels 172, 244 begin at the leftmost end of the base 168, as illustrated in FIG. 16, the upper channels 172 extend only approximately one-half of the overall length of the base 168, while the lower channels 244 extend the entire length of the base 168. Further, as best seen in FIG. 14, a receptacle 248 is formed in a lower planar surface 252 of the base 168. The receptacle 248 accommodates the corresponding male "nub" 240 of the conductor component 164.

Figure 17:
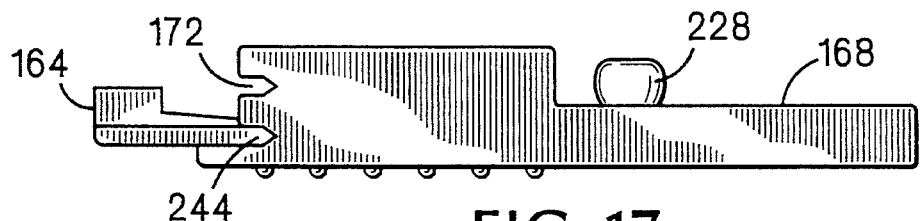
FIG. 17 Is a side view of the conductor component of FIGS. 11–13 partially assembled to the base of FIGS. 14–16.

Referring now to FIG. 17, there illustrated is a cross-sectional view of the conductor component 164 partially assembled to the base 168. The conductor component 164 is inserted into the opposing lower channels 244 of the base 168 such that portions of corresponding edges of the planar surface 236 of the conductor component 164 "ride" within the channels 244. The conductor component 164 is slid toward the rear of the base until the male "nub" 240 interfaces with the corresponding receptacle 248. The conductor component 164 completely assembled within the base 168 is illustrated in FIG. 18.

Figure 18:
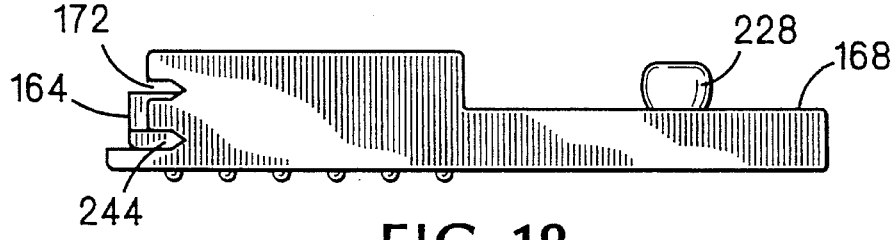
FIG. 18 is a side view of the conductor component of FIGS. 11–13 fully assembled to the base of FIGS. 14–16.
Figure 19:
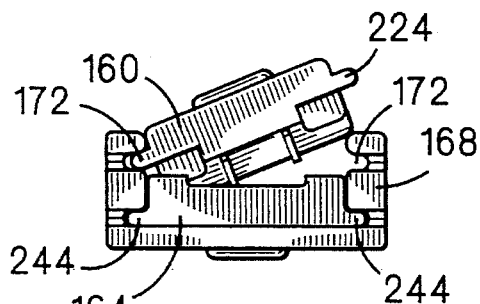
FIG. 19 is an end view of the slider of FIGS. 6–10 partially assembled to the base of FIGS. 14–16.
Figure 20:
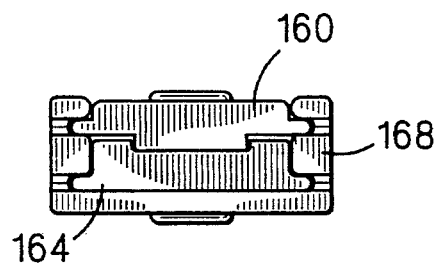
FIG. 20 is an end view of the slider of FIGS. 6–10 fully assembled to the base of FIGS. 14–16.

FIG. 19 illustrates an end view of the base 168 having the conductor component 164 completely inserted therein, in a similar manner to that of FIG. 18. FIG. 19 also illustrates an intermediate step in one method of assembly of the slider 160 within the opposing pair of upper channels 172 in the base 168. As shown, the left side of the flange 224 of the slider 160 is inserted into the corresponding left upper channel 172. Then, as illustrated in FIG. 20, the slider 160 is pressed down until the right side of the flange 224 is snapped into the corresponding right upper channel 172.

Figure 21:
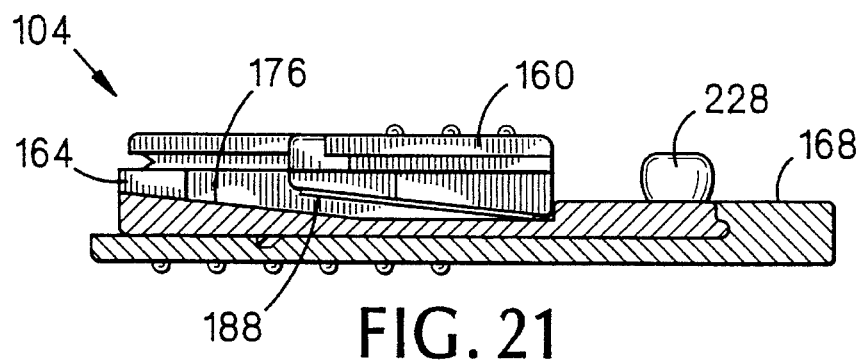
FIG. 21 is a cross-sectional view of the slider of FIGS. 6–10 shown in its open position.
Figure 22:
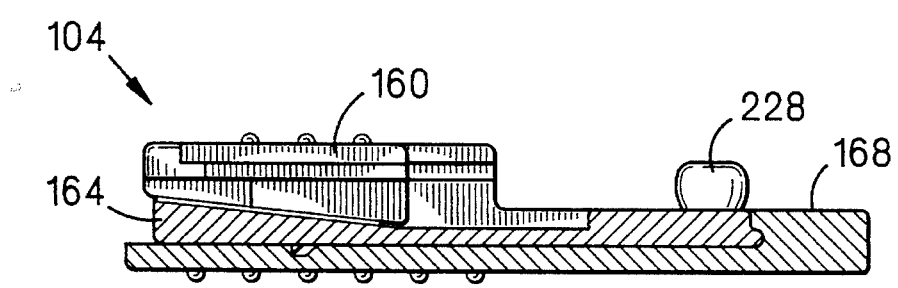
FIG. 22 is a cross-sectional view of the slider of FIGS. 6–10 shown in its closed position.

Referring now to FIG. 21, there illustrated is a cross-sectional view of the connector 104 fully assembled. FIG. 21 illustrates the slider pushed toward the rear end of the base 168. This is referred to as the "open" position of the slider 160. In such condition, the cavity 180 in the conductor component 164 is totally exposed (i.e., the cavity 180 is not covered by the slider 160). FIG. 22 illustrates the slider 160 in its closed position. That is, the slider 160 is slid along the opposing pair of upper channels 172 toward the front end of the base 168. FIGS. 21 and 22 serve to better illustrate, in cross-sectional form, the relationship between the inclined bottom surface 188 of the slider 160 and inclined surface 176 of the cavity 180.

Figure 23:
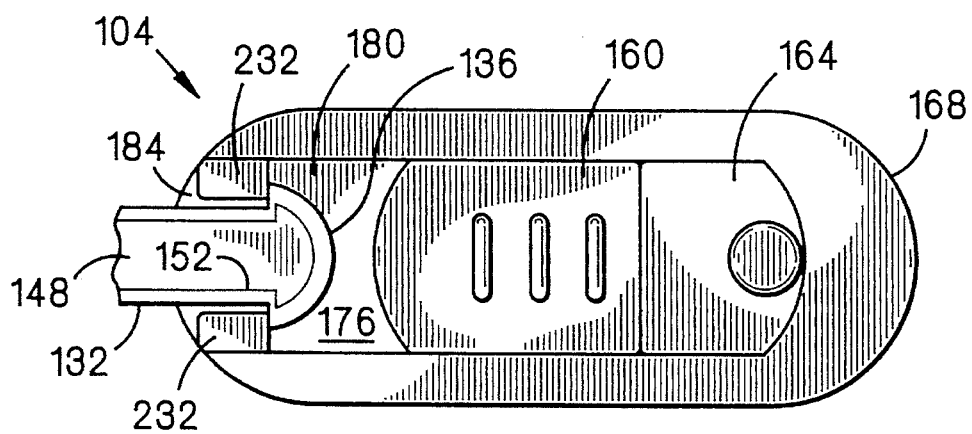
FIG. 23 is a top view of the slider of FIGS. 6–10 shown in its open position.

FIG. 23 is a top view of the assembled connector 104 that is similar in all respects to that of FIG. 21, with the exception that now the end portion 152 of the conductive component 140 of the electrode 100 (and corresponding stem end 136 of the foundation component 120) is inserted into the exposed cavity 180 of the conductor component 164 of the connector 104 such that the electrically-conductive end portion 152 is in electrical connection with the corresponding electrically-conductive surface 176 of the cavity 180. Further, the pathway portion 148 of the conductive component 140 of the electrode 100 (and corresponding stem portion 132 of the foundation component 120) is inserted into the narrower channel portion 184 of the cavity 180. As can be seen, the shapes and dimensions of the end portion 152 and pathway portion 148 of the conductive component 140 of the electrode 100, together with the corresponding shapes and dimensions of the cavity main portion 178 and narrow portion 184, are such that the electrode 100 cannot be removed from the cavity 180 by pulling on the electrode 100 in a leftward direction of FIG. 23. It is to be understood, however, that the end or head portion 152 of the conductive component 140 and the stem end or head 136 of the foundation component 120 are not limited to their semi-circular shapes. Other shapes may be utilized, if desired. It suffice that the end portion 152 and stem end 132 both have a shape that provides for a pair of shoulders 208, 256 (FIGS. 3, 4) that prevent the end portion 152 and stem end 136 from traveling through the narrow neck or channel portion 184 of the cavity 180.

Figure 24:
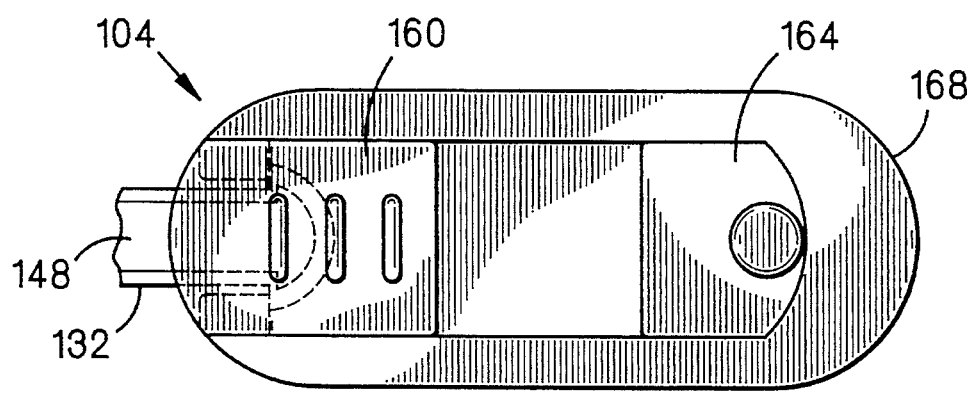
FIG. 24 is a top view of the slider of FIGS. 6–10 shown in its closed position.

FIG. 24 illustrates a top view of the connector 104 with the slider 160 positioned in its closed position. Note also that, with respect to FIGS. 1 and 3, the foundation component 120 of the electrode 100 covers completely the corresponding pathway and end portions 148, 152 of the electrode conductive component 140. Thus, when the pathway portion 148 and end portion 152 are inserted into the corresponding portions of the cavity 180 of the connector 104, the stem end 136 of the foundation component 120 helps to secure attachment of the electrode conductive component 140 to the connector conductor component 164, while the stem portion 132 of the foundation component 120 provides strength and protection to the portions of the conductive component 140 disposed on the underside of the stem portion 132 and stem end 136.

As the slider 160 is moved from its open to its closed position, the inclined bottom surface 188 of the slider 160 traps the end portion 152 of the conductive component 140 within the cavity 180. Then, as the slider 160 is continued on toward its closed position, the friction or pressure created by the two parallel inclined planes 176, 188 coming together provides a stationary electrical interface between the electrode 100 and the conductor component 164. As the slider 160 is moved toward its closed position, the two inclined planes 176, 188 interfere with each other, thereby distorting the electrode end portion 152 and stem end 136 slightly and providing a positive clamping effect for a secure electrical connection. The sliding motion which closes the slider 160 over the cavity 180 provides considerable amount of pressure on the electrode end portion 152 resulting in a firm, intimate electrical connection between the conductive surface of the end portion 152 of the electrode and the conductive surface 176 of the cavity 180. With the slider 160 now covering the cavity 180, the electrode end portion 152 is trapped within in the cavity 180, while the pathway portion 148 of the electrode conductive component 140 extends through the narrower cavity channel 184, which is too narrow for the end portion 152 of the electrode conductive component 140 to exit therethrough.

The amount of incline of both the bottom surface 188 of the slider 160 and the surface 176 of the cavity is typically less than ten degrees. However, the specific amount of incline is dependent upon the relative movement of the slider 160 and the thickness of the electrode end portion 152 together with the stem end 136 of the foundation component 120. As the slider 160 is moved toward its closed position, the slider 160 tends to try to climb out of the pair of opposing upper channels 172. However, it is prevented from doing so; therefore, a large amount of vertical compression force is forced downward onto the cavity surface 176 containing the electrode end portion 176. The pair of rails 226 on the bottom surface 188 of the slider 160 help to apply force to the electrode. Also, the nature of the sliding design tends to trap the electrode end portion 152 before distorting it somewhat with compression forces. It has been found that the relatively small amount of force in the range of one to two pounds applied to the slider 160 in moving it to its closed position results in approximately five hundred pounds of force being applied to the electrode end portion 152. As the slider 160 is moved to its closed position, the relatively narrower neck portion 196 of the bottom surface 188 of the slider 160 interfaces with the corresponding narrow portion 184 of the cavity 180 formed in the connector conductor component 164. Once the slider 160 has achieved its fully closed position, the amount of compressive forces tend to hold the slider 160 securely in place.

The friction interface between the parallel inclined planes 176, 188 holds the electrode interface between the electrode end portion 152 and the connector conductor component 164 in a stable, movement-free, reliable manner. This is because the application of physical force, such as a pull on the patient electrical cable attached to the connector 104 at the post 228, is passed through the connector components from the cavity interface to the electrode components. Since the physical strength provided by the electrode end portion 152 exceeds the strength of the electrode's adhesion to the skin of a patient, the connector design of the present invention provides a positive mechanical linkage necessary to prevent physical disconnects between the electrode 100 and the connector 104.

Figure 25:
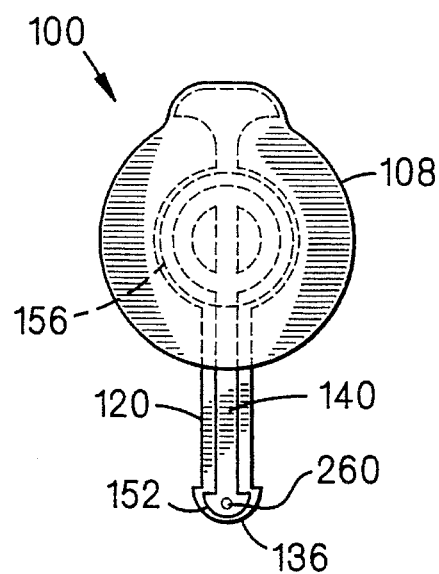
FIG. 25 is a top view of an alternative embodiment of the electrode of the present invention.
Figure 26:
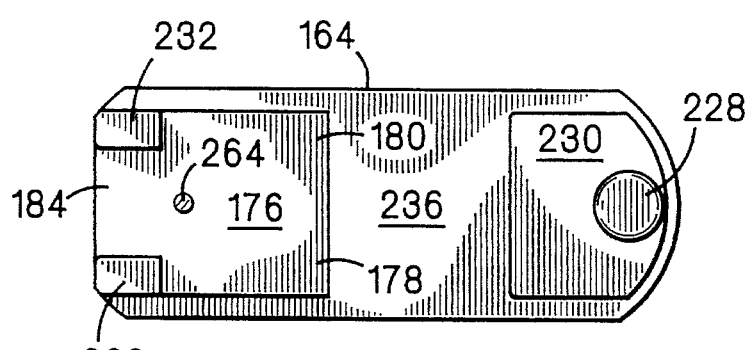
FIG. 26 is a top view of an alternative embodiment of the conductor component of the connector.

Referring now to FIGS. 25–28, there illustrated are several views of an alternative embodiment of the electrode 100 of the present invention. Specifically, FIG. 25 illustrates an alternative embodiment of the electrode 100 of FIG. 1 wherein now a small throughbore or hole 260 is formed completely through both the conductive component 140 of the electrode 100 at its end portion 152 and also through the corresponding stem end 136 of the foundation component 120. For simplicity and ease of understanding, like reference numerals will be used to disclose similar elements described and illustrated in FIGS. 1–24 in the preferred embodiment described hereinbefore. FIG. 26 illustrates a top view of an alternative embodiment of the conductor component 164 of the connector 104. The conductor component 164 differs from that described hereinbefore in the preferred embodiment in that a small post 264 is formed which protrudes from the upper inclined surface 176 of the cavity 180.

Figure 27:
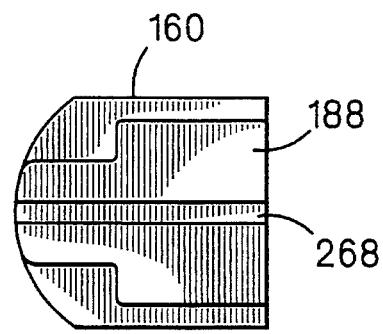
FIG. 27 is a bottom view of an alternative embodiment of the slider component of the connector.
Figure 28:
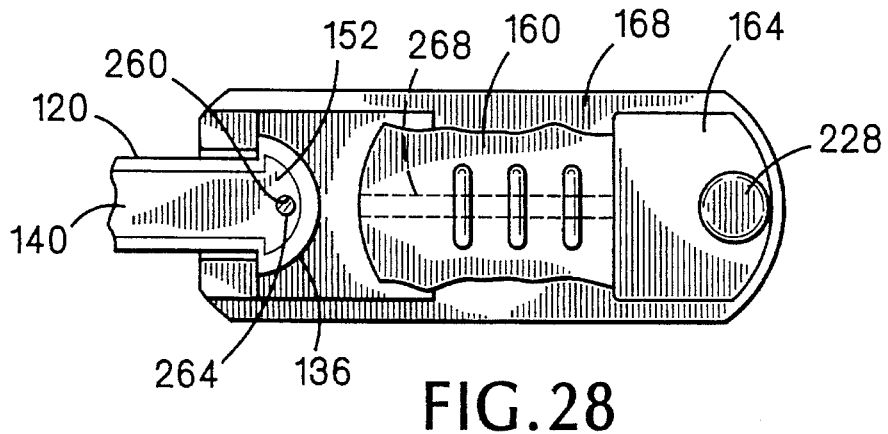
FIG. 28 is a top view of an alternative embodiment of the electrode of FIG. 25 assembled to the conductor component of FIG. 26, illustrating the slider of FIG. 27 in its open position.

FIG. 27 illustrates a bottom view of the slider 160 of this alternative embodiment. The bottom surface 188 of the slider is an inclined plane. Formed in the center of the bottom surface 188 is a groove 268 which extends the entire length of the bottom surface 188. With the slider 160 attached to the base 168 and conductor component 164 of the alternative embodiment, as illustrated in FIG. 28, the slider 160, when moved to its closed position, mates with the inclined plane 176 of the cavity 180 in a similar fashion to that described hereinbefore with the preferred embodiment. The groove 268 formed in the bottom surface 188 of the slider 160 moves past the additional post 264 to which the electrode end portion 152 is attached.

In assembling the electrode 100 to the connector 104, the electrode 100 is removed from the release liner 200 and applied to the skin of a patient at a desired location. The end portion 152 of the conductive component 140 of the electrode 100 is then inserted into the open cavity 180 of the connector 104. The slider 160 is moved from its open to its closed position to provide a secure interface to the electrode 100. A wire (not shown) is attached to the post 228 of the conductor component 164. The wire transmits any sensed electrical signals to a medical instrument (not shown) such as an electrocardiograph.

The electrode 100, because of its relatively flat construction and low profile, extends substantially parallel to the person's skin. Thus, the greatest component of any typical force directed against the electrode 100 will be directed as a shear force operating on the interface between the electrode 100 and the skin. Any tugging force applied to, e.g., the connector 104 or wire, is not likely to result in separation of the electrode from the skin. Thus, a typical tugging force applied by a patient is converted to a shear force which is unlikely to cause the electrode 100 to unadhere from the person's skin. Such shear forces are provided primarily by the design of the top component 108 of the electrode. The top component 108 may be of any suitable shape which provides a required shear force to prevent the electrode 100 from becoming unadhered from the patient's skin.

The connector has been described as comprising three components: a slider 160, a conductor component 164 and a base 168. Instead, the conductor component 164 and the base 168 may be formed as one piece. However, since the base 168 typically contacts the skin, the conductive portion of such one piece design must be limited, for safe and proper operation, to the inclined planar surface 176 of the cavity 180, the main planar surface 236, and the post 228. This may be accomplished, for example, by fabricating the entire piece out of non-conductive material, and applying a conductive material, such as by lamination to the surfaces 176, 236 and post 228.

It should be understood by those skilled in the art that obvious structural modifications can be made without departing from the spirit of the invention. Accordingly, reference should be made primarily to the accompanying claims, rather than the foregoing specification, to determine the scope of the invention.

Having thus described the invention, what is claimed is:

1. A biomedical electrode for sensing an electrical signal on the skin of a human or for impinging an electrical signal through the skin of a human, comprising:

a. a foundation component having a pair of opposing sides, a first side adapted to face the skin and a second side adapted to face away from the skin, the foundation component comprising a flexible material, the foundation component including:

i. a top portion for facilitating the removal of the electrode from a carrier sheet, for facilitating the holding of the electrode while positioning the electrode on the skin, and for facilitating the removal of the electrode from the skin;

ii. a center portion connected to the top portion;

iii. a stem portion connected to the center portion and extending away from the center portion; and iv. a head portion disposed at an end of the stem portion, at least a part of the held portion being larger in width than a width of the stem portion;

b. a conductive component that is electrically-conductive and has a pair of opposing sides, a first side adapted to face the skin and a second side adapted to face away from the skin, the conductive component including:

i. a sensor portion whose second side is disposed adjacent to and in an abutting relationship to the center portion on the first side of the foundation component;

ii. a neck portion integrally connected with the sensor portion and whose second side is disposed adjacent to and in an abutting relationship to the stem portion on the first side of the foundation component; and iii. a head end portion integrally connected with the neck portion and whose second side is disposed adjacent to and in an abutting relationship to the head portion of the first side of the foundation component, at least a part of the head end portion being larger in width than a width of the neck portion; and c. a conductive media that is electrically-conductive and is disposed adjacent to and in abutting contact with the first side of at least a portion of the sensor portion of the conductive component.

2. The electrode of claim 1, further comprising a top component having a pair of opposing sides, a first side adapted to face the skin and a second side adapted to face away from the skin, at least a portion of the second side of the foundation component being disposed adjacent to and in butting contact with the first side of the top component.

3. The electrode of claim 2, wherein at least a portion of the first side of the top component has one or more adhesives coated thereon, wherein at least a portion of the one or more adhesives coated on the first side of the top component is operable to adhere to the skin to secure the electrode thereto.

4. The electrode of claim 3, wherein at least one of the one or more adhesives coated on the first side of the top component is electrically-conductive.

5. The electrode of claim 3, wherein at least one of the one or more adhesives coated on the first side of the top component is non electrically-conductive.

6. The electrode of claim 1, wherein the flexible material for the foundation component is selected from the group consisting of: (i) polyester; (ii) polypropylene; and (iii) polyethylene.

7. The electrode of claim 2, wherein the top component is comprised of a material selected from the group consisting of: (i) a polyester film; (ii) a polypropylene film; (iii) a polyethylene film; (iv) a woven material; (v) a non-woven material; and (vi) a foam.

8. The electrode of claim 2, wherein the top component comprises patch means for providing adhesive shear forces when the electrode has a pulling force applied to it from any direction, thereby aiding in keeping the electrode securely adhesively affixed to the skin.

9. The electrode of claim 2, wherein the top component is dimensionally sized to cover the top portion and center portion of the foundation component at a minimum.

10. The electrode of claim 1, wherein the conductive component comprises a conductive ink applied to at least a portion of the first side of the foundation component.

11. The electrode of claim 10, wherein the conductive ink contains at least a component of silver.

12. The electrode of claim 1, wherein the stem portion of the foundation component has a width that is less than a width of the head portion of the foundation component at a juncture of the stem and head portions.

13. The electrode of claim 1, wherein the head end portion of the conductive component has a throughbore formed through an entire thickness of a material comprising the conductive component, and wherein the head portion of the foundation component has a corresponding throughbore formed through an entire thickness of a material comprising the foundation component, and aligned with the throughbore formed in the conductive component.

14. The electrode of claim 1, wherein the conductive media has adhesive properties for adhering to the skin.

15. The electrode of claim 1, wherein the conductive media comprises an electrically-conductive path adapted to be disposed next to the skin.

16. A biomedical electrode comprising:
a. a foundation component having a first side adapted to face an area of skin when the electrode is applied thereto, and having an opposing second side adapted to face away from the skin, the foundation component including:
  i. a top portion that comprises means for facilitating the placement of the electrode on the skin and the removal of the electrode from the skin;
  ii. a center portion integrally connected with the top portion;
  iii. a stem portion integrally connected with the center portion and extending away from the center portion; and
  iv. a head portion integrally connected with the stem portion at an end thereof, at least a part of the head portion being larger in width than a width of the stem portion; and
b. a conductive component that is electrically-conductive and is applied to the first side of the foundation component to cover at least a portion thereof, at least a portion of the conductive component having a conductive media adapted to be disposed next to the skin, wherein the conductive component includes:
  i. a sensor portion disposed adjacent to and in an abutting relationship to the center portion on the first side of the foundation component;
  ii. a neck portion integrally connected with the sensor portion and disposed adjacent to and in an abutting relationship to the stem portion on the first side of the foundation component; and
  iii. a head end portion integrally connected with the neck portion and disposed adjacent to and in an abutting relationship to the head portion of the first side of the foundation component, at least a part of the head end portion being larger in width than a width of the neck portion.

17. The electrode of claim 16, further comprising a top component having a first side adapted to face the skin and an opposing second side adapted to face away from the skin, at least a portion of the second side of the foundation component being disposed adjacent to and in abutting contact with the first side of the top component.

18. The electrode of claim 17, wherein at least a portion of the first side of the top component has one more adhesives coated thereon, wherein at least a portion of the one or more adhesives coated on the first side of the top component is operable to adhere to the skin to secure the electrode thereto.

19. The electrode of claim 18, wherein the top component comprises means for providing adhesive shear forces when the electrode has a pulling force applied to it, thereby aiding in keeping the electrode securely adhesively attached to the skin.

* * * * *